United States Patent [19]
Jensen

[11] Patent Number: 5,091,057
[45] Date of Patent: Feb. 25, 1992

[54] STRIPPING PROCESS FOR WATER REMOVAL FROM ALCOHOL

[75] Inventor: Wayne D. Jensen, Magnolia, Ark.

[73] Assignee: Ethyl Corporation, Richmond, Va.

[21] Appl. No.: 555,105

[22] Filed: Jul. 20, 1990

[51] Int. Cl.$^5$ .......................... B01D 3/00; C07C 29/80
[52] U.S. Cl. ........................ 203/18; 203/29; 203/33; 203/37; 203/39; 203/47; 203/81; 203/82; 568/916; 570/246
[58] Field of Search ................ 203/18, 19, 39, 47, 203/49, 63, DIG. 19, DIG. 11, 81, 82, 71, 33, 36, 37; 568/913, 916; 570/246

[56] References Cited

U.S. PATENT DOCUMENTS

| | | |
|---|---|---|
| Re. 16,267 | 2/1926 | Stevens .......................... 203/18 |
| 2,081,189 | 5/1937 | Wiezerich ........................ 203/18 |
| 2,582,214 | 1/1952 | Twigg ............................ 568/916 |
| 3,558,727 | 1/1971 | Jenkner et al. .................. 570/246 |
| 3,689,371 | 9/1972 | Kerber et al. ................... 203/18 |
| 4,309,254 | 1/1982 | Dahlstrom et al. ................ 203/19 |
| 4,358,346 | 11/1982 | Shinskey ......................... 203/19 |
| 4,358,536 | 11/1982 | Thorsson et al. ................. 203/19 |
| 4,783,563 | 11/1988 | Taniuchi et al. ................. 570/246 |
| 4,952,503 | 8/1990 | Granstedt ........................ 203/19 |

Primary Examiner—Wilbur Bascomb, Jr.
Attorney, Agent, or Firm—David E. LaRose

[57] ABSTRACT

A process for obtaining a substantially dry alcohol from a mixture comprising alcohol and water in a non-azeotropic amount by utilizing at least a portion of the alcohol in the mixture as the stripping medium.

20 Claims, 1 Drawing Sheet

STRIPPING PROCESS FOR WATER REMOVAL FROM ALCOHOL

BACKGROUND

This invention relates to a novel stripping process for the removal of water from mixtures containing alcohol and water.

Heretofore, drying of alcohol, i.e. the removal of water from alcohol water mixtures has been accomplished by distillation and/or stripping or adsorption operations among others. Distillation requires a significant amount of energy input, and depending on the impurities present, may require multiple steps.

Stripping or adsorption of water from alcohols using a dry vapor or liquid solvent typically requires a separate vessel for generation or regeneration of the vapor or solvent. Regeneration of the solvent provides for removal of water and/or impurities from the solvent so that it can be reused. Dry vapors for use in adsorption of water from alcohols may be generated by heating an essentially water-free solvent until it vaporizes. Typically, the dry vapor or solvent, while compatible with the alcohol to be dried, will be handled in spatially separate equipment thus requiring additional vessels for vaporization and regeneration operations. If the solvent or dry vapor is used only once, then disposal or waste treatment facilities must be provided. There is a need therefore for a facile economic means for drying a mixture containing alcohol and water in an non-azeotropic amount without the need for extensive solvent recovery processes.

SUMMARY OF THE INVENTION

This invention relates to a novel process for obtaining a substantially dry alcohol from a mixture comprising alcohol and water by utilizing at least a portion of the alcohol in the mixture to perform the drying operation.

DETAILED DESCRIPTION OF THE INVENTION

Figure 1:
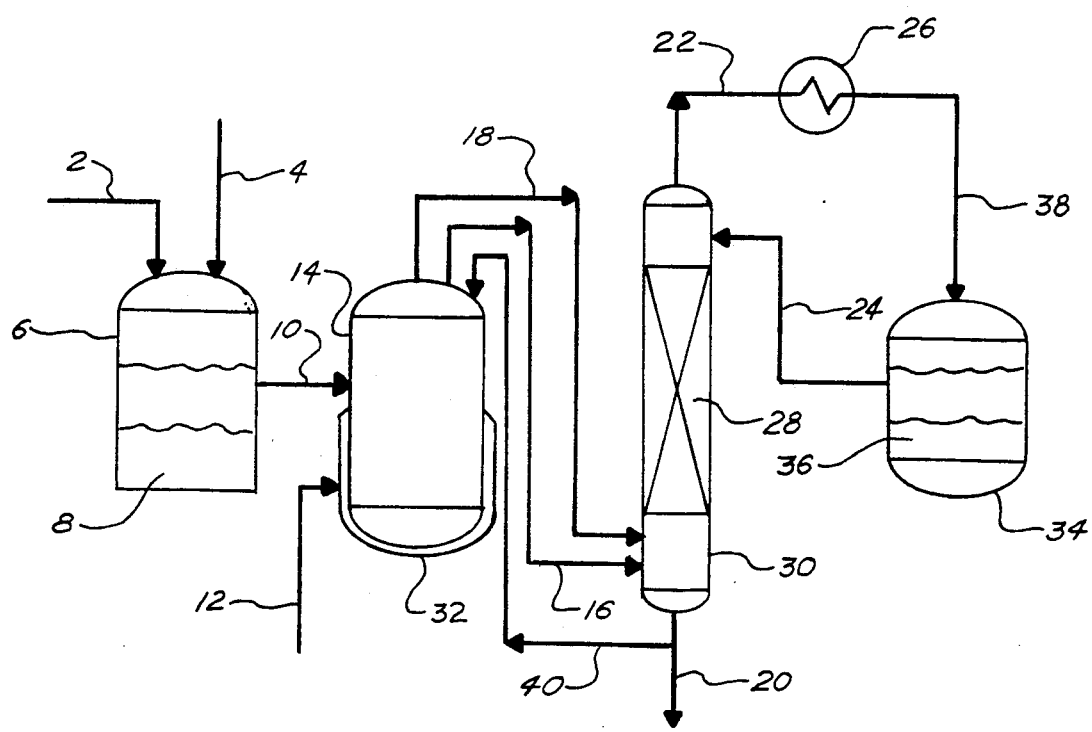
FIG. 1 is a schematic drawing not to scale of the apparatus for alcohol recovery and drying according to one embodiment of the invention.

This invention provides a process for recovery of a substantially dry alcohol product from a liquid mixture which mixture contains predominantly alcohol and water in a non-azeotropic amount, the process comprising: a) heating the liquid mixture so as to obtain a first vapor containing an alcohol portion and a water portion; b) condensing the first vapor to yield an alcohol phase and a water phase, the alcohol phase containing a minor amount of water to be removed; c) continuing to heat the liquid mixture so as to obtain a second vapor consisting essentially of alcohol; and d) contacting the alcohol phase from step (b) with the second vapor from step (c) so as to strip essentially all of the water from the alcohol phase thereby yielding the substantially dry alcohol product.

This process has particular application in the recovery and drying of alcohols used as solvents for the preparation of halogenated organic compounds using a batch or semicontinuous process. Typically, the solvent acts as a reaction medium for the halogenation reaction and is selected on the basis of solubility of the reactants and products in the solvent. Once the halogenated product is formed, the product is separated from the solvent and the solvent undergoes a series of operations for purification so that it can be reused in a subsequent batch. One operation is the neutralization of the solvent with an aqueous basic solution to decrease the amount of hydrohalic acid in the solvent. Hydrohalic acid is a byproduct of the halogenation reaction. Until now, it was difficult to recover a sufficient amount of dry solvent after neutralization without the use of a distillation column to remove water from the solvent. This invention provides for the first time, a facile economic method for recovery of substantially dry solvent without the need for a separate distillation operation.

In another embodiment, this invention relates to a process for producing a hexabromocyclododecane product using isobutanol as a solvent wherein the isobutanol is recovered from the reaction medium and subsequently dried, the process comprising: a) separating the hexabromocyclododecane product from the isobutanol and collecting the isobutanol as a centrate; b) neutralizing the centrate with an aqueous basic solution so as to form a first isobutanol phase containing less than an azeotropic amount of water and a first aqueous phase, c) separating the first isobutanol phase from the first aqueous phase; d) heating the first isobutanol phase so as to obtain a first vapor containing an isobutanol portion and a water portion; e) condensing the first vapor to yield a second isobutanol phase and a second water phase, the second isobutanol phase containing less than about 15 weight percent water; f) continuing to heat the first isobutanol phase so as to obtain a second vapor consisting essentially of isobutanol; and g) contacting the second isobutanol phase from step (e) with the second vapor from step (f) so as to strip essentially all of the water from the second isobutanol phase thereby yielding a substantially dry isobutanol.

The process of this invention provides a means for the recovery of a substantially dry alcohol product from a liquid mixture which mixture contains alcohol and water in a non-azeotropic amount. The alcohol that is recovered and dried is preferably a lower aliphatic alcohol (e.g. a $C_1$–$C_8$ alcohol), preferably a butanol or propanol, and most preferably isobutanol.

In a preferred embodiment, the liquid mixture is comprised predominantly of the alcohol (e.g. at least about 70 weight percent alcohol). The mixture may also contain up to about 20 weight percent of other impurities and at least about 5 weight percent water. The other impurities may be one or more halogenated aliphatic compounds; esters of aliphatic alcohols; aromatic compounds; cycloaliphatic compounds; halogenated aliphatic, cycloaliphatic or aromatic compounds and the like.

In the most preferred embodiment of the invention the liquid mixture contains less than an azeotropic amount of water. For example, when the alcohol is isobutanol, the liquid mixture contains less than about 33 weight percent water. If the mixture contains more than an azeotropic amount of water, during the generation of the first vapor an azeotropic mixture of alcohol and water will generally be formed as the amount of water in the mixture decreases. It is less desirable for the mixture to contain an azeotropic amount of water because of the difficulty in separating the water from the alcohol.

At process initiation, the liquid mixture is heated for a period of time and at a temperature which are sufficient to yield a first vapor. The first vapor is comprised of an alcohol portion and a water portion. As the vapor is formed it is condensed in a spatially separate vessel thereby reducing the amount of water initially in the liquid mixture. The temperature required to yield the first vapor is dependant on the alcohol mixture and the operating pressure. When the alcohol is isobutanol, a temperature of at least 80° .C is needed to form the first vapor at atmospheric pressure. Preferably the temperature is in a range of from about 85° C. to about 104° C. and most preferably from about 90° C. to about 100° C.

Once formed, the first vapor is condensed and collected in the spatially separate vessel. When the first vapor is condensed, there is provided an alcohol phase and a water phase. The alcohol phase contains a minor amount of water which is to be removed by contact with a dry alcohol vapor. The minor amount of water may be in a range of from about 3 weight percent up to but not including an azeotropic amount of water. Thus when the alcohol is isobutanol, the minor amount of water ranges from about 3 weight percent to about 30 weight percent and typically from about 6 weight percent to about 20 weight percent.

Subsequent to forming the first vapor, heating of the liquid mixture is continued so as to obtain a second vapor which consists essentially of the alcohol. Preferably this second vapor contains less than about 5 weight percent water and may contain a minor amount of other impurities. Most preferably, the second vapor contains less than about 3 weight percent water. The other impurities, which are in a minor amount include one or more of the beforementioned impurities which may vaporize from the liquid mixture with the alcohol. The temperature to which the liquid mixture is heated to form the second vapor is dependent on the pressure and the boiling point of the alcohol in the liquid mixture. When the alcohol is isobutanol, the temperature is preferably above about 104° C. Most preferably the temperature is in a range of from about 105° C. to about 110° C. Higher temperatures may be used, however at higher temperatures the vapors may contain more impurities than desired.

Pressure is not critical to the process of this invention. The process of this invention can be performed at pressures ranging from subatmospheric to superatmospheric. It is more desirable and less costly to use atmospheric pressure for the process of this invention.

Once the second vapor is formed, it is contacted with the alcohol phase previously condensed from the first vapor. The contact preferably takes place in a stripping operation and most preferably in a countercurrent stripping operation. The stripping operation provides a means for obtaining a substantially dry alcohol by removing from the liquid alcohol phase essentially all of the water dissolved in that phase. Thus, by providing a second vapor flow consisting essentially of alcohol, the water content can be reduced in the liquid alcohol phase obtained from the first vapor. Since the alcohol drying medium is comprised of at least a portion of the alcohol solvent to be recovered, there is less need for separate handling or collection facilities for the drying medium after its contact with the liquid alcohol phase in the stripping column. Likewise, there is less need for a separate distillation operation for recovery of the drying medium.

In a particularly preferred embodiment, the process of the invention is used for the recovery and drying of isobutanol used as a solvent in the bromination of cyclododecatriene for the production of hexabromocyclododecane (HBCD). HBCD is produced generally in accordance with the procedure as described in Jenkner et al. U.S. Pat. No. 3,558,727 incorporated herein by reference.

Accordingly, in the process for producing HBCD, cyclododecatriene is charged to a reaction vessel containing the solvent and an amount of bromine in excess of the stoichiometric amount needed to produce HBCD. The cyclododecatriene is then brominated so as to form HBCD in the form of crystals which can be readily separated from the solvent and reagents by conventional means such as filtration, centrifugation, settling, decantation and the like. In a preferred embodiment, the HBCD crystals are separated from the solvent by centrifugation yielding a centrate containing the solvent and soluble impurities. One impurity of particular importance is hydrobromic acid (HBr). In order to simplify the selection of materials of construction for the solvent handling and purification, the centrate is neutralized with an aqueous basic solution in order to neutralize substantially all of the hydrobromic acid.

Referring now to FIG. 1, a typical means for purification and drying of the solvent is illustrated.

The solvent which is separated from the HBCD product is collected as a centrate 2 in vessel 6. An aqueous basic solution 4 is then added to neutralize the centrate. The neutralized centrate has a pH of from about 6.8 to about 8.0. The aqueous basic solution may be comprised of an alkaline earth metal hydroxide or carbonate such as NaOH, KOH, LiOH, $Na_2CO_3$, or an ammonium compound such as $NH_4OH$. Preferably a sodium carbonate solution is used. The sodium carbonate solution may have a concentration in a range of from about 10 weight percent to about 22 weight percent $Na_2CO_3$.

To provide for neutralization of the centrate, the vessel contents are preferably mixed or agitated for a period of time sufficient to neutralize essentially all of the centrate. The vessel contents can be mixed by use of an agitator or by recirculating the vessel contents through a pump with or without the use of a mixing eductor.

After neutralizing the centrate, the agitation/or mixing is ceased and the vessel contents are allowed to settle. A first organic phase 10 can be separated from the first aqueous phase 8 for purification and drying. The first organic phase 10 should contain less than an azeotropic amount of water, which for isobutanol is less than about 33 weight percent water. Typically this first organic phase contains from about 8 to about 10 weight percent of dissolved water and may contain up to about 20 weight percent water.

After separating the first organic phase 10 from the first aqueous phase 8, the first organic phase is charged to a vessel 14 for heating so as to obtain a first vapor 16. The heating can be done by any conventional means such as an external heating jacket 32 attached to the exterior of the vessel 14. Other means for heating can be used such as internal heating coils or an external heat exchanger. The heating medium 12 applied to the heating jacket 32 may be steam, hot oil, or other heating medium which provides sufficient heat to vaporize at least a portion of the first organic phase 10.

Once formed, the first vapor in stream 16 passes through stripping column 30, and is condensed in condenser 26. There is preferably no stripping operation being performed during this step of the process. Passing the first vapor through the stripping column is a preferred method of collecting the first vapor since it reduces the amount of piping and equipment necessary to collect and condense the first vapor. Other means for collecting and condensing the first vapor prior to the stripping step are within the scope of this invention.

The condensate 38 from the first vapor is collected in vessel 34. In vessel 34, a second organic phase 24 and a second aqueous phase 36 are formed. The second organic phase 24 is recycled to the stripping column wherein water is removed from the organic phase by countercurrent contact with dry vapor 18. The dried solvent 20 can then be collected and reused in the production of another batch of HBCD.

A drying medium or adsorbant for removing water from stream 24 is provided by heating the first organic phase in vessel 14 until a second vapor stream 18 is formed which is substantially water free. This second vapor stream 18 provides the drying medium for stripping water from the recycle stream 24 as stream 24 is contacted by stream 18 in the stripping column.

In order to provide a sufficient amount of second vapor to dry the recycle stream 24, a portion of the dry solvent 40 is diverted to vessel 14. The amount of dry solvent 40 diverted to vessel 14 preferably provides a sufficient amount of second vapor 18 to dry essentially all of the recycle stream 24.

The stripping column 30 is an elongated substantially cylindrical enclosed chamber which functions as a contact tower. A portion of the chamber is filled with contact packing 28 which is held in place by conventional means. Any suitable contact packing may be used in the practice of the present invention. Typical packing materials include ceramic, certain metals, or various plastics.

While FIG. 1 represents one method for drying a solvent by using at least a portion of the solvent to perform the drying, variations in the process are possible. When operated in a batch or semi-continuous mode, stream 16 and stream 18 may flow through the same conduits, but at spatially separate times.

Once substantially all of the first organic phase has been vaporized and dried, the drying operation is discontinued until the next batch of centrate has been collected and neutralized.

Generally in accordance with the process of the invention, isobutanol initially containing from about 8 to about 10 weight percent water was dried such that it contained from about 2 to about 4 weight percent water. By adjusting the flows of recycle stream 24 and the rate of vaporization of the solvent in vessel 14, the amount of water in the stream 20 can be varied within a range of from about 1 weight percent water or less to about 10 weight percent water or more.

Variations in the process of this invention are within the spirit and scope of the appended claims.

I claim:

1. A process for recovery of a substantially dry alcohol product from a liquid mixture which mixture contains predominantly alcohol and water in a non-azeotropic amount, said process comprising:
    a) heating the liquid mixture so as to obtain a first vapor containing an alcohol portion and a water portion;
    b) condensing the first vapor to yield an alcohol phase and a water phase, the alcohol phase containing a minor amount of water to be removed;
    c) continuing to heat the liquid mixture so as to obtain a second vapor consisting essentially of alcohol; and
    d) contacting the alcohol phase from step (b) with the second vapor from step (c) so as to strip essentially all of the water from the alcohol phase thereby yielding the substantially dry alcohol product.

2. The process of claim 1 wherein the alcohol is isobutanol.

3. The process of claim 1 wherein the liquid mixture initially contains from about 6 to about 30 weight percent water.

4. The process of claim 1 wherein steps (a) through (d) are performed at essentially atmospheric pressure.

5. The process of claim 1 wherein the substantially dry alcohol contains less than about 5 weight percent water.

6. The process of claim 1 wherein the alcohol is isobutanol and the liquid mixture in step (a) is heated to a temperature in the range of from about 85° C. to about 104° C.

7. The process of claim 1 wherein the alcohol is isobutanol and the liquid mixture in step (c) is heated to a temperature in the range of from about 105° C. to about 115° C.

8. The process of claim 1 wherein a portion of the substantially dry alcohol product from step (d) is recycled so as to provide in step (c) a sufficient amount of second vapor to dry essentially all of the alcohol phase obtained in step (b).

9. A process for recovery of a substantially dry isobutanol from a liquid mixture which mixture contains from about 70 to about 93 weight percent isobutanol and from about 6 to about 30 percent water, said process comprising:
    a) heating the liquid mixture so as to obtain a first vapor containing an isobutanol portion and a water portion;
    b) condensing the first vapor to yield an isobutanol phase and a water phase, the isobutanol phase containing less than about 15 weight percent water;
    c) continuing to heat the liquid mixture so as to obtain a second vapor consisting essentially of isobutanol; and
    d) contacting the isobutanol phase from step (b) with the second vapor from step (c) so as to strip essentially all of the water from the isobutanol phase thereby yielding a substantially dry isobutanol.

10. The process of claim 9 wherein steps (a) through (d) are performed at essentially atmospheric pressure.

11. The process of claim 10 wherein the substantially dry isobutanol contains less than about 5 weight percent water.

12. The process of claim 11 wherein the liquid mixture in step (a) is heated to a temperature in the range of from about 80° C. to about 104° C.

13. The process of claim 12 wherein the liquid mixture in step (c) is heated to a temperature in the range of from about 105° C. to about 115° C.

14. The process of claim 13 wherein a portion of the substantially dry isobutanol from step (d) is recycled so as to provide in step (c) a sufficient amount of second vapor to dry essentially all of the isobutanol phase obtained in step (b).

15. In the production of a hexabromocyclododecane product using isobutanol as a solvent, a process for recovering and drying the isobutanol, said process comprising:

a) separating the hexabromocyclododecane product from the isobutanol and collecting the isobutanol as a centrate;
b) neutralizing the centrate with an aqueous basic solution so as to form a first isobutanol phase containing less than an azeotropic amount of water and an first aqueous phase;
c) separating the first isobutanol phase from the first aqueous phase;
d) heating the first isobutanol phase so as to obtain a first vapor containing an isobutanol portion and a water portion;
e) condensing the first vapor to yield a second isobutanol phase and a second water phase, the second isobutanol phase containing less than about 15 weight percent water;
f) continuing to heat the first isobutanol phase so as to obtain a second vapor consisting essentially of isobutanol; and
g) contacting the second isobutanol phase from step (e) with the second vapor from step (f) so as to strip essentially all of the water from the second isobutanol phase thereby yielding a substantially dry isobutanol.

16. The process of claim 15 wherein steps (a) through (g) are performed at essentially atmospheric pressure.

17. The process of claim 15 wherein the substantially dry isobutanol contains less than about 5 weight percent water.

18. The process of claim 15 wherein the liquid mixture in step (d) is heated to a temperature in the range of from about 80° C. to about 104° C.

19. The process of claim 15 wherein the liquid mixture in step (f) is heated to a temperature in the range of from about 105° C. to about 115° C.

20. The process of claim 15 wherein a portion of the substantially dry isobutanol from step (g) is recycled so as to provide in step (f) a sufficient amount of second vapor to dry essentially all of the second isobutanol phase obtained in step (e).

* * * * *

UNITED STATES PATENT AND TRADEMARK OFFICE
CERTIFICATE OF CORRECTION

PATENT NO. : 5,091,057                          Page 1 of 2

DATED      : FEBRUARY 25, 1992

INVENTOR(S) : WAYNE D. JENSEN

It is certified that error appears in the above-identified patent and that said Letters Patent is hereby corrected as shown below:

On the page under item 56 "References Cited," add the following:

U. S. PATENT DOCUMENTS
-- 3,544,641 12/70    Versnel ................... 570/246 --
-- 3,652,688 3/72     Olechowski et al .......... 570/246 --
-- 3,833,675 9/74     Newcombe et al ............ 570/246 --

FOREIGN PATENT DOCUMENTS
--   505,187 2/75     Japanese Pat.Off.                    --
-- 0,037,895 2/81     European Pat.Off.                    --
-- 3,120,621 12/82    Fed.Rep. of Germany                  --
-- 0,181,414 5/86     European Pat. Off.                   --
-- 2,205,830 12/88    United Kingdom                       --
-- 3,447,631 7/89     Fed.Rep. of Germany                  --

UNITED STATES PATENT AND TRADEMARK OFFICE
CERTIFICATE OF CORRECTION

PATENT NO.  : 5,091,057

DATED       : February 25, 1992

INVENTOR(S) : Wayne D. Jensen

It is certified that error appears in the above-identified patent and that said Letters Patent is hereby corrected as shown below:

OTHER PUBLICATIONS

-- Kirk-Othmer Encyclopedia of Chemical Technology, "Azeotropic and Extractive Distillation", Third Edition, Suppl. Volume, 1984, pages 145-158--.

Signed and Sealed this

Sixth Day of July, 1993

Attest:

Attesting Officer

MICHAEL K. KIRK

Acting Commissioner of Patents and Trademarks